Dec. 20, 1949. J. S. ARMSTRONG Plant Pat. 907
CAMELLIA PLANT
Filed Jan. 11, 1949
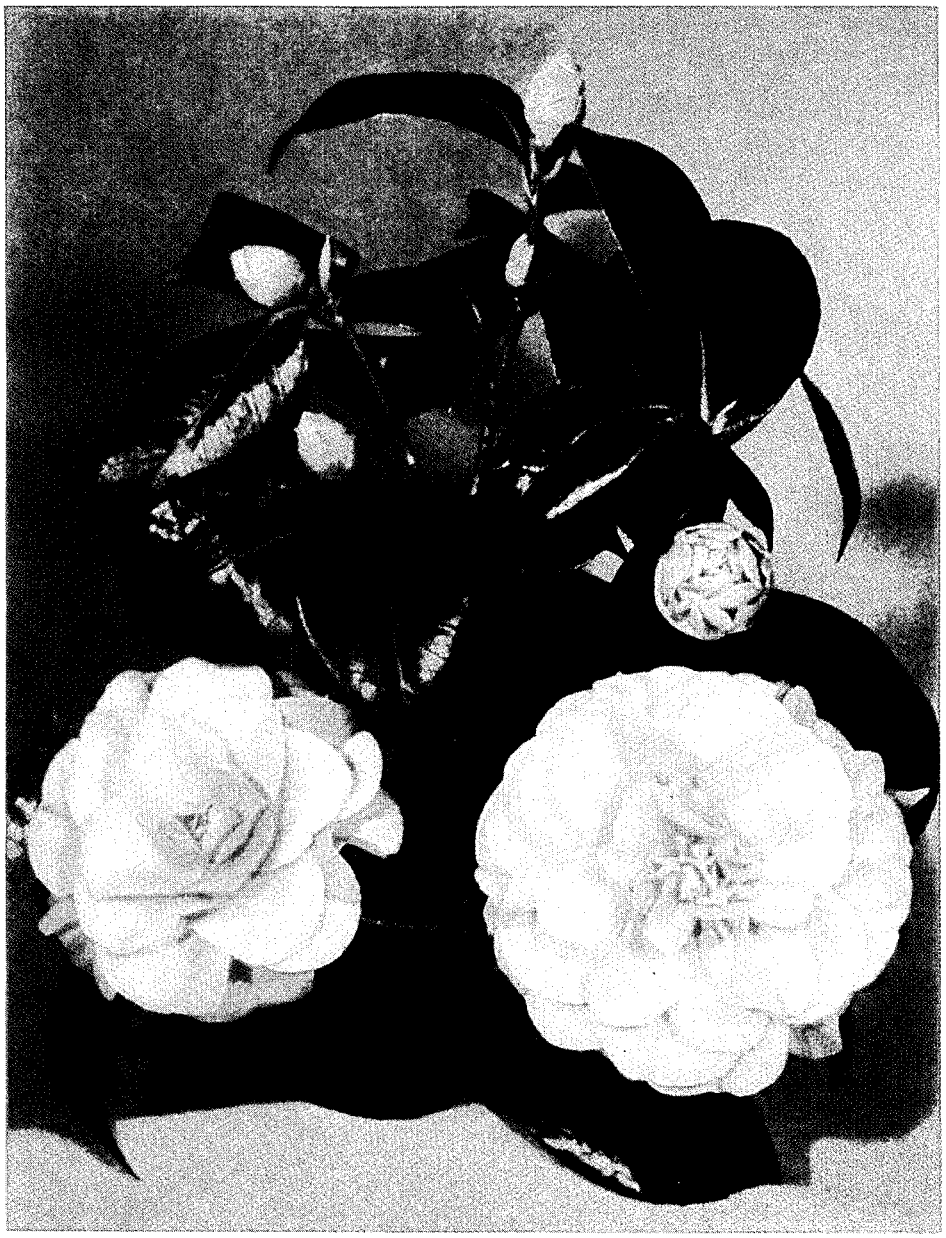
Inventor
John S. Armstrong
By Robbs & Robbs
Attorneys Patented Dec. 20, 1949

Plant Pat. 907

UNITED STATES PATENT OFFICE

907

CAMELLIA PLANT

John S. Armstrong, Ontario, Calif., assignor to Armstrong Nurseries, Inc., Ontario, Calif., a corporation of California Application January 11, 1949, Serial No. 70,291

1 Claim. (Cl. 47—60)

The present invention or discovery relates to a new and distinct variety of camellia plant, a seedling originated by a selection from a mixed lot of seedlings obtained by harvesting and growing seed from selected seed parents.

This new variety is characterized by a combination of novel characters best enumerated as follows:

(1) A plant bushy, upright, much branched in habit, abundantly furnished with dark green (substantially as described and illustrated) leaves of medium to large size and with a leathery, glossy upper surface texture making an attractive plant and a bountiful framework for the production of flowers.

(2) Flowers of a pleasing pink shade classified as to form as complete double, incomplete imbricated (American Camellia Society classification) with a graceful opening habit contributed to principally by the slight and gradual recurving of the petal tip, giving the flower a full high-centered appearance during the slow opening process.

(3) A season of bloom from January to March (in Southern California) during which, to the best of my knowledge, no other camellia variety of this color and form-type blooms.

(4) A flower medium in size and persistent to the stem, making it particularly suitable for use as a corsage flower.

Asexual reproduction of this new variety shows the foregoing characteristics come true to form and are established.

In the accompanying original drawing are illustrated specimens of the flower of this new variety in substantially full size and from closed bud to fully open flower with a background grouping of the foliage, showing its characters as nearly as possible true to shape, form, and color.

The following is a detailed description of the new variety, color terminology being in accordance with R. F. Wilson's Horticultural Colour Chart with exceptions noted from Ridgway's Color Standards and Nomenclature:

Type: Half hardy evergreen shrub for cut flowers and garden decoration.

Class: Hybrid seedling variety of *Camellia japonica.*

Propagation: Holds its distinguishing characteristics through succeeding propagations by cuttings and grafting.

*Flower*

Locality where grown: Ontario, California.

Flowers borne: Singly, sometimes two, axillary and terminal.

Quantity of bloom: Free, outdoors.

Continuity: One season, usually from January to March.

Fragrance: None.

Bud: Sessile.

*Before calyx breaks.—Size*—medium. *Form*—long, pointed, with tomentum on the surface of the bud. *Sepals*—imbricated, very broadly ovate in outline but strongly cupped about bud with sharp apical point, lower sepals becoming almost scale-like, and upper sepals becoming scarious when flower fully opens. *Color*—Biscay Green, Plate XVII (Ridgway), becoming Absinthe Green, Plate XXXI (Ridgway), at apex of bud, occasionally having a line margin of Rood's Brown, Plate XXVIII (Ridgway).

*As first petal opens.—Size*—medium. *Form*—flat at tip, but globular in general outline. *Color*—outside: Crimson, Plate 22/1, page 22; inside: Crimson, Plate 22/1, page 22. *Opening*—opens up well.

Bloom:

*Size.*—Medium; 8 to 9 cm. in diameter.

*Petalage.*—Very double; 38 to 44 petals arranged regularly with a tuft of 25 to 30 petaloids in center.

*Form.*—Complete double, incomplete imbricated; full high center; petals loosely rolled inward forming a broad U with slight and gradual recurving from center of petal to apex. (Classification as used by American Camellia Society.)

Petals: Moderately thick with inside satiny and outside somewhat shiny.

*Shape.*—Outside—obovate, with 1 to 2 notches. Intermediate—obovate, with 1 to 2 notches. Inside—oval, with 1 to 2 notches.

*Color.*—Colors may be modified by being margined, shaded, washed, or tinted with other colors.

This description of a newly opened flower was made from a camellia grown outdoors in the month of February, at Ontario, California:

*Color.—Outside petal*—outside surface: Neyron Rose, Plate 623, page 76, with margin of Neyron Rose, Plate 623/1, page 76; inside surface: Neyron Rose, Plate 623, page 76, with margin of Neyron Rose, Plate 623/1, page 76. *Intermediate petal*—outside surface: Neyron Rose, Plate 623/1, page 76, with narrow margin of Neyron Rose, Plate 623/2, page 76; inside surface: Neyron Rose, Plate 623/1, page 76, with narrow margin of Neyron Rose, Plate 623/2, page 76. *Inner petal*—outside surface: Neyron Rose, Plate 623/1, page 76, with narrow margin of Neyron Rose, Plate 623/2, page 76; inside surface: Neyron Rose, Plate 623/1, page 76, with narrow margin of Neyron Rose, Plate 623/2, page 76.

*General color effect.*—Newly opened flower—Neyron Rose, Plate 623/1, page 76.

*Behavior.*—Persistent, holding on plant until flower becomes old.

*Flower longevity.*—Cut flowers grown outdoors kept at living-room temperatures, 6 days in February.

*Reproductive organs*

Stamens: Usually none.

Pistils: Usually none, but when present are rudimentary and distorted. Stamens and pistils usually differentiated into petaloids.

Seed pods: Not known to set seed pods due to poor development of pistil.

*Plant*

Foliage: Leaves alternate, simple, abundant; medium to large; leathery; glossy above, semi-glossy beneath.

*Size.*—5 to 7 cm. wide and 7 to 11 cm. long.

*Shape.*—Ovate-lanceolate, with apex acuminate; base obtuse to acute, occasionally rounded; margin simply shallow serrate.

*Midrib.*—Prominent, raised on upper and under surface of leaf.

*Veins.*—Pinnate, raised slightly on upper and under surface of leaf, but not prominent.

*Petiole.*—Medium length; 6 to 9 mm. long.

*Color.—Mature*—upper surface: near Yew Green, Plate XXXI (Ridgway); under surface: between Rainette Green, Plate XXXI (Ridgway), and Light Cress Green, Plate XXXI (Ridgway). *Young*—upper surface: near Calla Green, Plate V (Ridgway); under surface: near Lettuce Green, Plate V (Ridgway).

Growth:

*Habit.*—Bushy; upright; much branched.

*Growth.*—Moderately heavy; vigorous.

*Main stems.*—Color—near Vandyke Brown, Plate XXVIII (Ridgway), becoming scurfy when several years old.

*Branches.*—Color—Sayal Brown, Plate XXIX (Ridgway), shaded with Saccardo's Umber, Plate XXIX (Ridgway).

*New shoots.*—Color—near Lettuce Green, Plate V (Ridgway).

I claim:

A new and distinct variety of camellia plant characterized as to novelty by its bushy, upright, much branched habit of growth; abundance of dark green, medium sized foliage with leathery, glossy upper surface texture; by the flowers of pink shade, complete double, incomplete imbricated type with graceful opening habit and having the appearance, due to its slow opening process, of a full high-centered bloom; by its season of bloom and by the medium size flower, persistent to stem making it particularly suitable for use as a corsage flower, substantially as shown and described.

JOHN S. ARMSTRONG.

No references cited.